US005511674A

United States Patent [19]
Boyd et al.

[11] Patent Number: 5,511,674
[45] Date of Patent: Apr. 30, 1996

[54] ACCESSORY TRAY FOR USE IN SURGERY

[76] Inventors: William E. Boyd; Lynn D. Boyd, both of 424 Mac La., Muskegon, Mich. 49445

[21] Appl. No.: 166,683

[22] Filed: Dec. 14, 1993

[51] Int. Cl.[6] ..................................................... A47F 7/00
[52] U.S. Cl. .................... 211/70.6; 211/86; 206/363; 206/557
[58] Field of Search ................ 211/86, 88, 70.6, 211/126; 248/129, 127, 158, 161, 145; 206/363, 557, 562

[56]     References Cited

U.S. PATENT DOCUMENTS

| | | | |
|---|---|---|---|
| 1,658,891 | 2/1928 | Gauck | 211/86 |
| 1,974,213 | 9/1934 | Gilbert | 211/88 |
| 2,839,201 | 6/1958 | Auster | 211/86 |
| 3,186,673 | 6/1965 | Olson | 211/86 X |
| 3,301,406 | 1/1967 | Scott | 211/88 |
| 3,539,204 | 11/1970 | Keller | 281/45 |
| 3,949,880 | 4/1976 | Fortunato | 211/86 |
| 4,501,403 | 2/1985 | Goodrich | 248/443 |
| 4,715,573 | 12/1987 | Lieger | 248/129 |
| 4,728,065 | 3/1988 | Coote | 211/70.6 X |
| 5,078,280 | 1/1992 | Nordeen | 211/86 |
| 5,170,804 | 12/1992 | Glassman | 128/849 |

*Primary Examiner*—Robert W. Gibson, Jr.
*Attorney, Agent, or Firm*—Brooks & Kushman

[57]     ABSTRACT

An accessory tray for use in supporting surgical pads, the accessory tray adapted for connection to a surgical stand wherein the accessory tray comprises a support section having an outer surface for receiving the surgical pads, a connection section extending from the support section, the connection section including an attachment means for removably connecting the support section to the surgical stand wherein the support section is disposed at an acute angle in relation to the surgical stand.

17 Claims, 2 Drawing Sheets

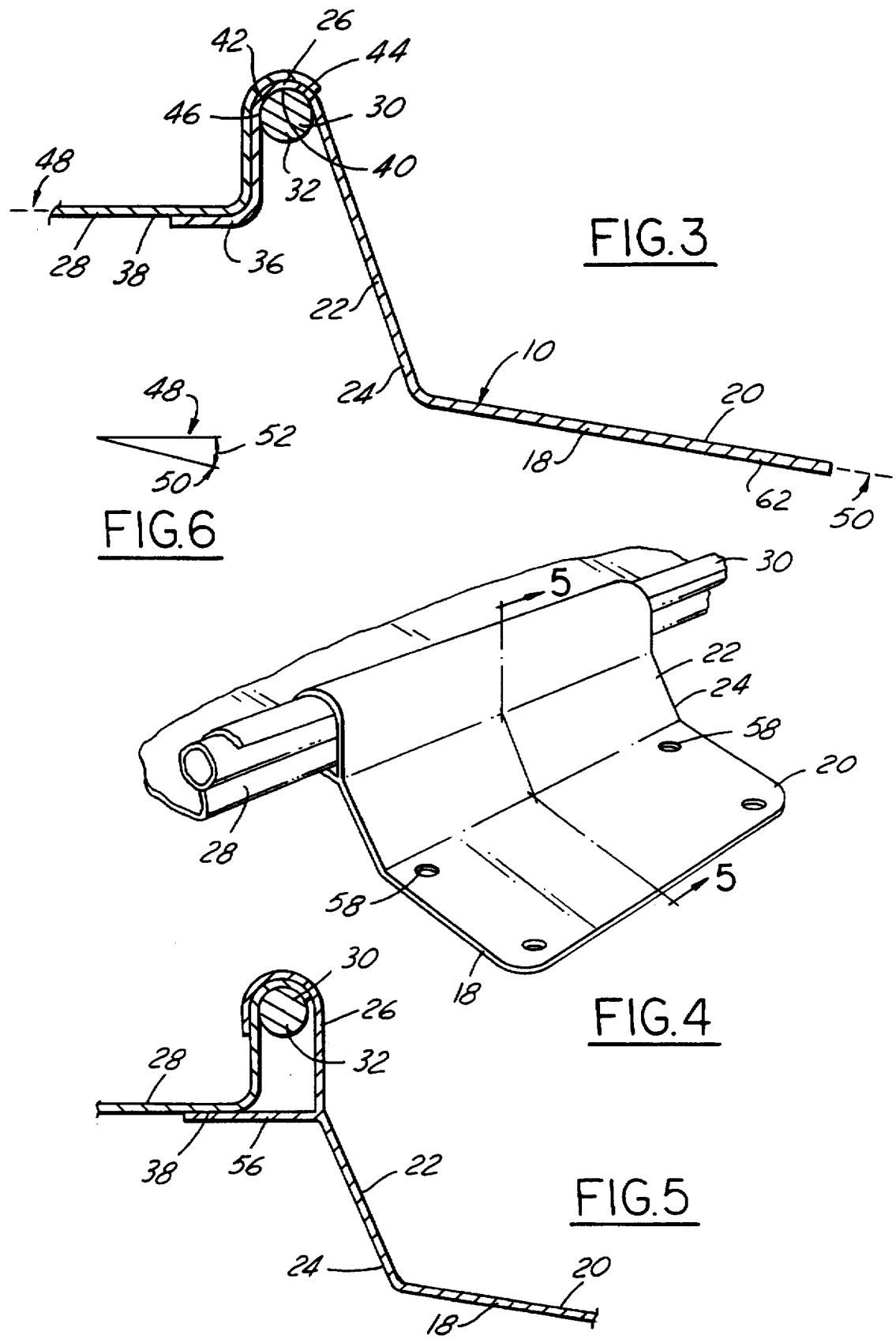

5,511,674

ACCESSORY TRAY FOR USE IN SURGERY

TECHNICAL FIELD

The present invention relates to accessory trays for use in surgery and, more particularly, to a sterilizable accessory tray for supporting absorbent material pads for use in neurosurgery.

BACKGROUND ART

Neurosurgery is surgery of the central nervous system which requires very delicate tissue to be dissected, retracted and possibly removed. As those skilled in the art will recognize, absorbent, protective pads of material, which are soaked in an anticoagulant or saline solution, are used to absorb or retain blood and other brain fluids that tend to accumulate during this dissection period of the surgery. These absorbent material pads conventionally utilize a length of sterilized string, twine, or the like for easy removal of the fluid-soaked absorbent pad from the surgical site.

As those skilled in the art will further recognize, neurosurgeons commonly use various types of medical instruments or bayonette-type forceps which include elongated members for allowing very precise manipulation of small objects and precise operating procedures. As such, the attached string or the like often used for location of the absorbent pad must be made of such a material that it is easily located and grasped by a conventional pair of forceps so that the neurosurgeon can remove the absorbent pad from the surgical area.

As neurosurgery is a procedure where efficient technique is critical and time is particularly important, it is necessary to completely prepare and set up all supplies and accessories that are required by the neurosurgeon prior to surgery. For this reason, it is common for the operating room nurse or assistant to set up the absorbent pads in such a way as to allow the neurosurgeon to quickly grasp with the forceps the particular absorbent pads that are required as needed. Thus, it is known to those skilled in the art to utilize a substantially planar plate to layout the absorbent pads prior to surgery.

This plate is commonly manufactured from a plastic material and is essentially a flat rectangular plate including spaced elongate ribs that protrude from one side of the plate. These ribs are utilized to separate the absorbent pads from each other. In addition, it is known to simply use sterilized pieces of cardboard, small basins, or to simply place the absorbent materials out on conventional surgical trays. The absorbent pads come in a variety of different sizes, lengths and shapes for use in conjunction with different areas of the surgical site which have different space limitations.

It is known that these conventional means for supporting the various absorbent pads cause special problems for the neurosurgeon during surgery. Specifically, the absorbent pads of various shapes and size must be laid out in such a fashion as to be easily viewed and grasped by the neurosurgeon during surgery. Application of the absorbent pads on a flat surface situated adjacent the operating table does not provide the most easily viewable location of the absorbent pads. This placement is not ergonomically acceptable to neurosurgeons who must grasp these pads with only the use of forceps or medical instruments.

In addition, it is known that the long attachment strings that are required with the absorbent materials become tangled and intertwined with each other if the particular support plate that is used to support the absorbent pads is too short or crowds the absorbent materials closely together. Lastly, the current support plates do not afford any way of holding or easily accessing the various types of forceps which are used in conjunction with the absorbent pads. Thus, the neurosurgeon or his assistant must often search through the operating equipment tray for the particular forceps used to insert and remove the absorbent pads from the surgical site.

These and other problems associated with the prior art are solved by the accessory tray of the present invention.

SUMMARY OF THE INVENTION

It is an object of the present invention to provide an accessory tray for use in holding surgical pads where the accessory tray is adapted to be connected to a surgical stand and the accessory tray comprises a support section having an outer surface for receiving the surgical pads and a connection section extending the support section including an attachment means for removably connecting the support section to the surgical stand where the support section is disposed at an acute angle in relation to the surgical stand.

It is another object of the present to provide an accessory tray as described above wherein the accessory tray attachment means includes a first section which extends from the support section and a second section extending from the first section which is configured to be disposed between a surgical tray supported on the surgical stand and a cross-member of the surgical stand for supporting the accessory tray from the surgical stand.

It is still another object of the present invention to provide an accessory tray as described above further comprising a third section which extends from the second section and is configured to abuttingly engage at the bottom surface of the surgical tray.

It is yet another object of the present invention to provide an accessory tray as described above wherein the extending cross-member of the surgical tray has a circular cross-section and the second section of the support section defines a connection cavity having an annular cross-section whereby the cross-member is cooperatively receivable within the connection cavity.

It is still yet another object of the present invention to provide an accessory tray as described above wherein the support section and connection section are integrally formed together, the support section and connection section have a uniform thickness, and the accessory tray is manufactured from sterilizable stainless steel or plastic materials.

These and other objects, features and advantages of the present invention will become apparent from a review of the description, claims and drawings.

BRIEF DESCRIPTION OF THE DRAWINGS

FIG. 3 is a cross-section taken along lines 3—3 of FIG. 1;

FIG. 4 is a fragmentary perspective view of an alternative embodiment of the present invention;

FIG. 5 is a cross-section of the present invention taken along lines 5—5 of FIG. 4; and FIG. 6 s a diagrammatical view of the angle defined by the support section of the present invention in relation to a surgical tray of FIG. 3.

BEST MODE FOR CARRYING OUT THE INVENTION

Figure 1:
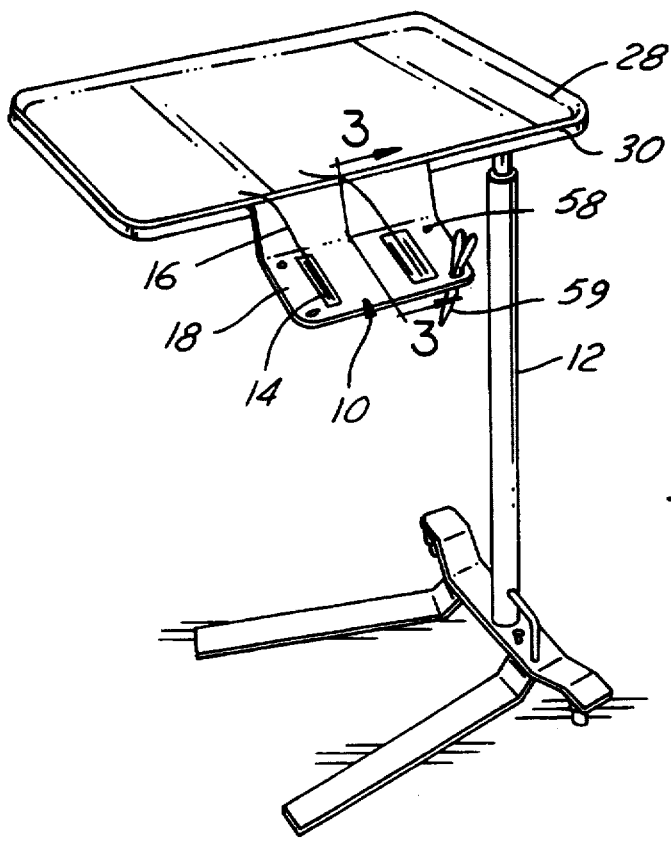
FIG. 1 is a perspective view of the accessory tray of the present invention shown in use with a conventional surgical stand and tray.

Referring to FIG. 1 there is shown generally the accessory tray 10 of the present invention. Accessory tray 10 is shown attached to surgical stand 12. Surgical pads 14 are shown along with the attached removal strings 16 positioned for use atop accessory tray 10.

Figure 2:
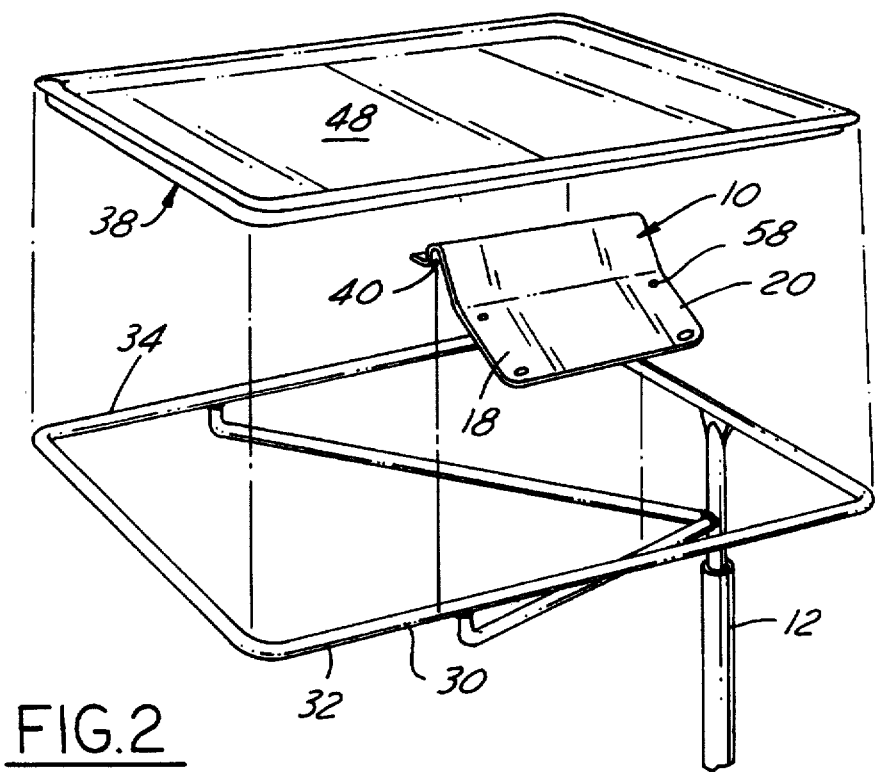
FIG. 2 is an exploded perspective view of the accessory tray of the present invention showing the accessory tray disposed between the surgical tray and cross-member of the surgical stand.

Referring to FIGS. 2 and 3, the accessory tray 10 includes a support section 18 having an outer surface 20 for receiving the surgical pads as illustrated in FIG. 1. A connection section 22 extends from support section 18. Connection section 22 has a straight first section 24 extending from connection section 22 and a curved second section 26 extending from said first section 24.

The second section 26 is configured to extend between the surgical tray 28 and cross member 30 of surgical stand 12. As those in the art will recognize, surgical stands commonly used in surgery include a rectangular frame 32 having cross members 30 and 34 disposed to support the surgical tray as illustrated in FIG. 2. Thus second section 26 is designed to extend or be positioned directly between cross member 30 and tray 28.

In the preferred embodiment shown in FIGS. 1–3, a third section 36 extends from second section 26. Third section 36 is configured to abuttingly engage the bottom surface 38 of surgical tray 28. In the manner illustrated in FIGS. 1—3, accessory tray 10 is removably supported by attachment to cross member 30 and with the bottom surface 38 of surgical tray 28.

More specifically, cross member 30 has a circular cross section 32 and second section 26 defines a connection cavity 40. Connection cavity 40 has an annular cross section 42 which is configured to cooperatively receive circular cross section 32. The outer surface 44 of cross member 30 is in direct contact with the inner surface 46 of the second section 26 which defines the connection cavity 40.

As can be seen from FIG. 1, the support section 18, when operatively connected to the surgical stand 12, defines an acute angle with respect to the surgical stand. Specifically, the surgical tray 28 as supported on the surgical stand defines a first plane 48 and the support section 18 defines a second plane 50 as illustrated in FIG. 3. First plane 48 further defines an angle 52 with respect to second plane 50 as shown in the diagram of FIG. 6. The preferred embodiment of the present invention has an angle 52 in a range from 0 to 45 degrees with the most preferred angle being 10 degrees.

An alternative embodiment of the present invention is illustrated in FIGS. 4 and 5. This alternative embodiment is similar to the embodiment described above and differs relative to the placement of the accessory tray 10 in relation to the surgical tray 28. As can be seen from FIGS. 4 and 5, the surgical tray is placed directly over the cross member 30 and the accessory tray 10 is then placed over both the cross member 30 and surgical tray 28. In this embodiment, a support ridge 56 extends from the first section 24 of the tray 10 towards the surgical tray 28. Support ridge 56 abuttingly engages the bottom surface 38 of surgical tray 28 in a similar fashion to third section 36 as described above.

Both alternative embodiments may include apertures 58 for receiving forceps 59. The apertures can be arranged as shown in FIGS. 1,2 and 4 on opposite sides of support section 18. Although four apertures 58 are shown in the drawings, it is understood that any number can be provided.

The accessory tray is preferably manufactured from a disposable plastic material used only for one surgical procedure. It is contemplated that the accessory tray may be manufactured from any sterilizable metal or plastic material. If desired, the accessory tray alternatively could be made of an integral sheet of sterilizable stainless steel having a uniform thickness.

The accessory tray of the present invention, as described above, provides a means for supporting surgical absorbent pads for surgical procedures which are ergonomically angled for easy viewing by the surgeon. The absorbent pads can be laid out in an orderly fashion prior to surgery to increase the efficiency of the surgeon during the operation.

The relatively open space defined by the support section 18 allows the absorbent pads to be laid out in a manner such that the various pads shapes and sizes are easily recognizable. Preferably, the accessory tray of the present invention is also sterilizable. It is further easily removable and affixable to conventional surgical stands.

In addition, the accessory tray may be used without being affixed to a surgical stand. The accessory tray may be completely inverted and placed on any surface including the patient's chest during surgery. The absorbent surgical pads 14 are then disposed on surface 62 in a similar manner to their placement on surface 20.

While the best mode for carrying out the invention has been described in detail, those familiar with the art to which this invention relates will recognize alternative designs and embodiments for practicing the invention as defined by the following claims.

What is claimed is:

1. An accessory tray in combination with a surgical stand for supporting surgical pads, the surgical stand having a surgical tray defining a first planar surface, said accessory tray comprising:

a support section having an outer surface for receiving said surgical pads;

a connection section extending from said support section, said connection section including an attachment means for removably connecting said support section to said surgical stand wherein said support section is disposed at an acute angle in relation to said surgical tray planar surface.

2. The combination as in claim 1 wherein said surgical stand includes an extending cross member and said surgical tray has a bottom surface whereby said surgical tray is supported by said cross member and said attachment means comprises a first section extending from said support section and a second section extending from said first section configured to extend between said surgical tray and said cross member.

3. The combination claim 1 wherein said connection section further comprises a third section which extends from said second section and is configured to abuttingly engage said bottom surface of said surgical tray.

4. The combination as in claim 1 wherein said surgical stand includes an extending cross member and said attachment means comprises a first section extending from said support section including a support ridge which extends towards said surgical tray from said first section and is configured to abuttingly engage the bottom surface of said surgical tray and a second section also extending from said first section configured to extend over both said surgical tray and said cross member and directly engage said surgical tray.

5. The combination as in claim 1 wherein said acute angle is in a range of between 2.5 and 35 degrees.

6. The combination as in claim 1 wherein said extending cross member has a circular cross section and said second section defines a connection cavity having an annular cross section whereby said cross member is cooperably receivable within said connection cavity.

7. A sterilizable accessory tray for use in supporting surgical pads, said accessory tray adapted for connection to a surgical stand having a cross member and a surgical tray supported on said cross member, said surgical tray having a first planar surface, said accessory tray comprising:

a support section for receiving said surgical pads, said support section defining a second planar surface;

a planar connection section extending from said support section;

an attachment section extending from said connection section, said attachment section adapted to removably connect said connection section to the surgical stand, said attachment section having a cavity adapted to mate with the cross member on the surgical stand; and said support section having at least one aperture for holding a medical instrument.

8. An accessory tray for use in supporting surgical pads, said accessory tray adapted for connection to a surgical stand, said surgical stand including an extending cross member and a surgical tray having a generally planar surface supported by said cross member, said accessory tray comprising:

a support section having an outer surface for receiving said surgical pads;

a connection section extending from said support section, said connection section including an attachment member for removably connecting said support section to said surgical stand, said attachment member comprising a first section extending from said support section and a second section extending from said first section adapted to be positioned between said surgical tray and said cross member for connecting said support section to said cross member, wherein said support section is disposed at an acute angle in relation to said planar surface of the surgical tray.

9. An accessory tray as in claim 1 wherein said connection section further comprises a third section which extends from said second section and is configured to abuttingly engage the bottom of said generally planar surface of said surgical tray.

10. An accessory tray as in claim 1 wherein said generally planar surface comprises a surgical tray and said support section extends from said connection section at an acute angle from said generally planar surface in a range of between 2.5 and 35 degrees.

11. An accessory tray as in claim 1 wherein said extending cross member has a circular cross section and said second section defines a connection cavity having an annular cross section whereby said cross member can be cooperably receivable within said connection cavity.

12. An accessory tray as in claim 1 wherein said support section includes at least one aperture configured to receive medical forceps.

13. An accessory tray as in claim 1 wherein said support section includes a first aperture disposed on one side of said support section and a second aperture disposed on an opposite side of said support section wherein said apertures are configured to receive medical forceps.

14. An accessory tray as in claim 1 wherein said support section and connection section are integrally formed together.

15. An accessory tray as in claim 1 wherein said support section and connection section have a uniform thickness.

16. An accessory tray as in claim 1 manufactured from stainless steel.

17. An accessory tray as in claim 1 manufactured from a plastic material.

* * * * *

UNITED STATES PATENT AND TRADEMARK OFFICE
CERTIFICATE OF CORRECTION

PATENT NO. : 5,511,674
DATED : April 30, 1996
INVENTOR(S) : Boyd et al

It is certified that error appears in the above-indentified patent and that said Letters Patent is hereby corrected as shown below:

Column 2, line 19, after "extending" insert -- from --.

Signed and Sealed this

Tenth Day of December, 1996

Attest:

BRUCE LEHMAN

Attesting Officer

Commissioner of Patents and Trademarks